United States Patent [19]

Gatti

[11] Patent Number: 4,629,729

[45] Date of Patent: Dec. 16, 1986

[54] ENDOWED WITH ANTI-VIRAL ACTIVITY 2-ALKYLAMINO-4,6-DIHALO PYRIMIDINES

[76] Inventor: Daniele Gatti, Via Sacco & Vanzetti, 3, 27020 Travacò Siccomario, Italy

[21] Appl. No.: 763,767

[22] Filed: Aug. 8, 1985

Related U.S. Application Data

[63] Continuation of Ser. No. 598,922, Apr. 10, 1984, abandoned.

[30] Foreign Application Priority Data

May 6, 1983 [IT] Italy .............................. 20960 A/83

[51] Int. Cl.$^4$ .................. A61K 31/505; C07D 239/02
[52] U.S. Cl. ..................................... 514/275; 544/330
[58] Field of Search ........................ 544/330; 514/275

[56] References Cited

U.S. PATENT DOCUMENTS 3,259,623 7/1966 Kober ................................. 544/330
3,991,190 11/1976 Garzia et al. ....................... 424/251

OTHER PUBLICATIONS

Lugari et al, Chem. Abst. 100:1110u.
Mossini et al, Chem. Abst. 92:1542q.
Loiseau et al, Chem. Abst. 82:156376f.
Mossini et al, Ateneo Parmense, Acta. Nat., 15(1979) 39–48.

Primary Examiner—Mark L. Berch
Assistant Examiner—Cecilia Shen
Attorney, Agent, or Firm—Stevens, Davis, Miller & Mosher

[57] ABSTRACT

The invention relates to new pyrimidine derivatives endowed with anti-viral activity, to the method for the preparation thereof and to the pharmaceutical compositions containing them. Pyrimidine derivatives of the invention are useful for the treatment of animals and human patients infected with viruses.

10 Claims, No Drawings

2-ALKYLAMINO-4,6-DIHALO PYRIMIDINES ENDOWED WITH ANTI-VIRAL ACTIVITY

This application is a continuation, of application Ser. No. 598,922, filed 4/10/84, now abandoned.

The present invention relates to new pyrimidine derivatives endowed with anti-viral activity.

More particularly, the pyrimidine derivatives of the present invention are comprised in the following general formula:

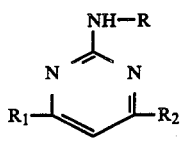

wherein R is an alkyl group containing from 1 to 6 carbon atoms; $R_1$ and $R_2$, equal or different, are Cl, Br or I.

Pyrimidine derivatives of the present invention can be used both in veterinary and human field for treating animals or human patients infected with viruses.

Therefore, a further object of the present invention are the pharmaceutical compositions containing the new pyrimidine derivatives as active ingredient.

It is known (Experientia 29 (1973), 1442-1443; 1559-1561 and 30 (1974), 1272) that 2-amino-4,6-dichloropyrimidine is effective to inhibit the growth of polio-virus in vitro by interfering with the intracellular assembly of the components of the viral particle, but it is ineffective for treating virus infections in vivo, because aminoacids such as cysteine, cystine and glutamine, which are always present, interfere with the pyrimidine.

The derivatives of the present invention have the peculiarity of acting on the viral aynthesis, not on the host cell.

The cell synthetizes the nucleic acid (DNA or RNA), synthetizes the viral protein; however, in the presence of the derivatives of the present invention, both nucleic acid and protein are unable to assembly to give a new infecting virus.

The pyrimidine derivatives here described are endowed with the property to penetrate the cell in an amount sufficient to inhibit viral replication. This fact is due to the alkyl group which substitutes a hydrogen atom of the amino group.

The pyrimidine derivatives of this invention are not anti-metabolites in that they are not antagonized by metabolite precursors. Furthermore, the derivatives of the present invention act both on RNA viruses and DNA viruses but only on some of them. In other words, they show a specificity although they are aspecific.

Among the RNA viruses, the pyrimidine derivatives of the present invention are effective on Picorna virus, in particular on polio-virus, on Coxsackie virus, on ECHO virus. Among the DNA viruses they are effective on Herpes virus and Pox virus (vaccinia).

From U.S. Pat. No. 3,991,190 are known derivatives of 2-amino-4,6-dichloropyrimidine substituted in position 2 by an acetyl or by a formyl group. These derivatives have the disadvantage to penetrate the cell in such a restricted amount to undergo the inhibiting action of the aminoacids, always present, such as cysteine, cystine, glutamine, etc.

On the contrary, the pyrimidine derivatives of the present invention enter the cell in a remarkable amount, thus blocking the inhibiting action of the above mentioned aminoacids.

When used in the veterinary field, the pyrimidine derivatives which are the object of the present invention are expecially effective against Marek's disease, very dangerous in that contagion spreads very easily; Marek's disease, at present, is prevented by vaccination. However, it is known that effectiveness of vaccines against Marek's disease is very limited because of the resistance phenomenon (Congr. Chemoth., Tokyo 2, 33, (1969); Virology 28, 707, (1966). The pyrimidine derivatives of the invention do not cause resistance phenomena, because of their action mechanism.

In human field, these compounds are particularly useful for the therapeutic treatment of viral diseases against which no vaccines are known or for which the use of vaccines is particularly disadvantageous.

2-Butylamino-4,6-dichloro-pyrimidine, in particular, has proved to be particularly useful in treating diseases caused by *Herpes genitalis* and for treating herpetic keratitis.

A further object of the present invention is the method for the preparation of the derivatives of the general formula (I).

More particularly, the synthesis of the new pyrimidine derivatives is carried out according to the following scheme:

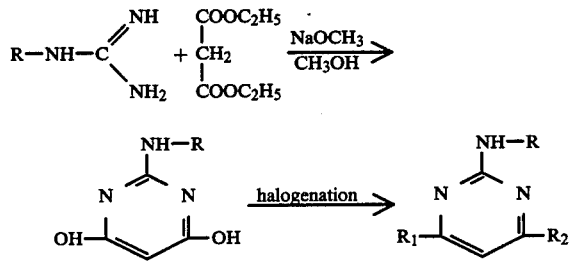

The starting material, guanidine, is prepared according to the method described in Org. Synth. 22, 59, (1942); J. Org. Chem. 13 (1950), 924. The halogenation of the derivatives occurs according to known methods. Chlorination is, for instance, carried out by $POCl_3$.

In the veterinary application, the pyrimidine derivatives of the invention are administered by oral route, mixed with fodder, or by I.m. injections.

The doses to be administered to the animals are as follows:

10-20 mg/kg twice a day, by oral route;
20-50 mg/kg/day by a single i.m. injection.

The pharmaceutical compositions for the administration to human patients may be formulated as soft gelatine capsules, tablets, emulsions or vials for i.m. injections.

The generally used pharmaceutically acceptable excipients and/or vehicles may be added to the active ingredient.

The doses for the administration to human patients are as follows:

10-20 mg/kg, twice a day, by oral route
20-50 mg/kg/day by a single i.m. injection.

Pharmaceutical compositions formulated as ointments, creams, collyria, powders for topic use are also foreseen. In this case, the amount of the active ingredient in the pharmaceutical composition is 1–5%.

The following examples are given to illustrate the present invention, but they do not limit it in any way.

EXAMPLE 1

Preparation of the 2-methylamino-4,6-dichloropyrimidine. 1 mol of methylguanidine (73 g) and 1 mol of diethylmalonate (160 g) are boiled under reflux for 3 hours with 1.3 mol of sodium methoxide in 1000 ml of methanol, under anhydrous conditions and while stirring.

The mixture is evaporated to dryness, the residue is treated with 1000 ml of water and acidified with acetic acid. After having dried in vacuo, the whole is crystallized at 50° C. from ethanol. The dioxiderivative is obtained with a yield of 80% on the theory 1 mol of the dioxiderivative prepared as described above (141 g), 5 mols of $POCl_3$ and 1000 ml of anhydrous benzene are boiled under reflux for 2 hours, while stirring.

After having distilled to about 1/5 of the initial volume, the mixture is poured on minced ice (200 g). The temperature is allowed to reach the room temperature; thereafter, the mixture is filtered, washed with water, dried at 60°–70° C. under vacuum and finally is crystallized from ethanol.

115 g of 2-methylamino-4,6-dichloropyrimidine (yield 65% on the theoretic) are thus obtained. m.p. 157°–158° C.

The analysis confirms the structure of the product.

EXAMPLE 2

Preparation of 2-butylamino-4,6-dichloropyrimidine 1 mol of butylguanidine (115 g) and 1 mol of diethylmalonate (160 g) are boiled under reflux for 3 hours with 1.3 mol of sodium methoxide in 1000 ml of methanol under anhydrous conditions and while stirring.

The mixture is evaporated to dryness, the residue is treated with 1000 ml of water and acidified with acetic acid. After having dried in vacuo, the whole is crystallized from ethanol, at 50° C. 1 mol of the dioxiderivative prepared as described above (183 g) 5 mols of $POCl_3$ and 1000 ml of anhydrous benzene are boiled under reflux for 2 hours, while stirring.

After having distilled under vacuum to about 1/5 of the initial volume the mixture is poured on minced ice (200 g). The temperature is allowed to reach the room temperature, the pH is adjusted to a value higher than 8 with $Na_2CO_3$ and then the whole is extracted three times with ether. The ether extracts are collected, the ether is distilled off. The residue is the 2-butylamino-4,6-dichloropyrimidine, in form of a pale yellow oil.

The analysis confirms the structure of the product.
Analogously there are prepared:
2-ethylamino-4,6-dichloropyrimidine; m.p. 63°–64° C.
2-isopropylamino-4,6-dichloropyrimidine in form of a pale yellow oil.

I claim:

1. A pharmaceutical composition for animal use consisting essentially of an anti-virally effective amount of a pyrimidine compound of the formula:

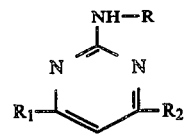

wherein R is an alkyl group having from 1 to 6 carbon atoms, and $R_1$ and $R_2$, individually selected, are Cl, Br or I, together with a pharmaceutically acceptable carrier.

2. A pharmaceutical composition according to claim 1, wherein the pyrimidine compound is 2-methylamino-4,6-dichloropyrimidine.

3. A pharmaceutical composition according to claim 1, wherein the pyrimidine compound is 2-butylamino-4,6-dichloropyrimidine.

4. A pharmaceutical composition according to claim 1, wherein the pyrimidine compound is 2-ethylamino-4,6-dichloropyrimidine.

5. A pharmaceutical composition according to claim 1, wherein the pyrimidine compound is 2-isopropylamino-4,6-dichloropyrimidine.

6. A method for treating an animal infected with a virus, wherein the virus is Picorna virus, polio virus, coxsackie virus, ECHO virus, herpes virus or pox virus, which comprises administering to the animal a pyrimidine compound of the formula:

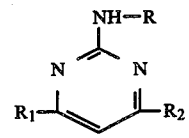

wherein R is an alkyl group having 1 to 6 carbon atoms, and $R_1$ and $R_2$, individually selected, are Cl, Br or I, in an amount effective to treat the infection.

7. A method according to claim 6, wherein the pyrimidine compound is administered orally.

8. A method according to claim 7, wherein the pyrimidine compound is administered at a dosage of 10–20 mg/kg.

9. A method according to claim 6, wherein the pyrimidine compound is administered by intramuscular injection.

10. A method according to claim 9, wherein the pyrimidine compound is administered at a dosage of 20–50 mg/kg.

* * * * *